US008486333B2

(12) United States Patent
Wang et al.

(10) Patent No.: US 8,486,333 B2
(45) Date of Patent: Jul. 16, 2013

(54) CENTRIFUGAL FLUID ANALYZER ROTOR

(75) Inventors: Mark Wang, Fremont, CA (US); Nan Zhang, Cupertino, CA (US)

(73) Assignee: MicroPoint Biosciences, Inc., Sunnyvale, CA (US)

( * ) Notice: Subject to any disclaimer, the term of this patent is extended or adjusted under 35 U.S.C. 154(b) by 863 days.

(21) Appl. No.: 12/321,359

(22) Filed: Jan. 16, 2009

(65) Prior Publication Data
US 2009/0227041 A1 Sep. 10, 2009

Related U.S. Application Data

(60) Provisional application No. 61/063,670, filed on Feb. 4, 2008.

(51) Int. Cl.
*A61M 1/00* (2006.01)

(52) U.S. Cl.
USPC ........... 422/45; 422/50; 422/500; 422/501; 422/502; 422/503; 422/68.1; 422/82.01

(58) Field of Classification Search
USPC ......... 422/99–100, 50, 68.1, 82.01, 500–503, 422/45
See application file for complete search history.

(56) References Cited

U.S. PATENT DOCUMENTS

| 3,795,451 | A |   | 3/1974  | Mailen            |
|-----------|---|---|---------|-------------------|
| 3,829,223 | A |   | 8/1974  | Hamel             |
| 4,225,558 | A |   | 9/1980  | Peterson et al.   |
| 4,244,916 | A |   | 1/1981  | Guigan            |
| 4,279,862 | A |   | 7/1981  | Bretaudiere et al.|
| 4,894,204 | A |   | 1/1990  | Cornut            |
| 4,898,832 | A |   | 2/1990  | Klose et al.      |
| 4,963,498 | A |   | 10/1990 | Hillman et al.    |
| 5,160,702 | A |   | 11/1992 | Kopf-Sill et al.  |
| 6,063,589 | A | * | 5/2000  | Kellogg et al. ........... 435/24 |

* cited by examiner

*Primary Examiner* — Jyoti Nagpaul
(74) *Attorney, Agent, or Firm* — Gary Baker; Quine Intellectual Propery Law Group, P.C.

(57) ABSTRACT

This invention provides rotors and methods of precisely metering a sample fluid and mixing the sample with a reagent. The rotors have a metering tube of defined volume that fills until sample flow is stopped by surface tension of a meniscus at a capillarity port, while excess sample is stripped from the metering tube inlet by centripetal force of the spinning rotor. By spinning the rotor at a higher speed, a reagent can be forced from a reagent chamber to contact the meniscus, breaking the surface tension and allowing the metered sample to mix with the reagent.

8 Claims, 18 Drawing Sheets

CENTRIFUGAL FLUID ANALYZER ROTOR

CROSS-REFERENCE TO RELATED APPLICATIONS

This application claims priority to and benefit of a prior U.S. Provisional Application No. 61/063,670, Centrifugal Fluid Analyzer Rotor, by Mark Wang, et al., filed Feb. 4, 2008. The full disclosure of the prior application is incorporated herein by reference.

FIELD OF THE INVENTION

The invention is directed to centrifugal fluid analysis rotors and methods that automatically proportion and mix two or more fluids in an analytical technique. Devices include a sample metering tube that holds a sample fluid at a capillary port to a mixing chamber, and reagent held at a capillary port at the mixing chamber. Spinning the rotor forces reagent into the chamber to contact the meniscus of the sample, causing the sample to flow and mix with the reagent in precise proportions in the chamber. Methods include rotating a rotor of the invention at a first rotational speed to precisely fill the sample fluid metering tube without spilling past the sample capillary port, then spinning the rotor at a higher speed to force reagent from the reagent chamber to contact the sample meniscus releasing the metered sample fluid to mix with the reagent in the mixing chamber.

BACKGROUND OF THE INVENTION

Biological tests of blood plasma and other biological fluids frequently require that fluids be quickly divided into predetermined volumes for analysis in a variety of optical tests or assays. It is also frequently desirable to separate potentially interfering cellular components of the material from the other fluid prior to testing. Such measurement and separation steps have typically been performed by centrifugation to separate, for instance, blood plasma from the cellular components, followed by manual or automated pipetting of predetermined volumes of the blood plasma into separate test wells. Such procedures are labor intensive and time-consuming. As a result, various automated systems and methods have been proposed for providing multiple aliquots of plasma suitable for testing in a more efficient manner.

A major advance in the analysis of biological fluids has been the use of centrifugal rotors. These rotors are designed to measure volumes of a biological fluid, such as blood, remove cellular components, and mix the fluid with appropriate diluents for analysis, for example by optical testing. Typically, the rotors provide a plurality of samples in separate cuvettes in which the samples can be optically analyzed. Prior art rotors have frequently utilized complex designs which are costly and difficult to manufacture. Often, the rotors require various separable parts, which must be brought together or separated at different points in the centrifugation procedure. Previous centrifugal rotors have often been limited in the number of discrete samples and test wells they can provide. In some cases, these rotors require use of a separate displacement fluid to effect flow of blood and plasma through the system.

Many analytical devices exist employing centrifugal force to transfer fluids between assay chambers. U.S. Pat. No. 4,244,916 discloses a rotor comprising a plurality of cuvettes positioned radially outward of a central receptacle. Each cuvette is connected to the central receptacle by a duct and comprises a separate air escape orifice. U.S. Pat. No. 4,314,968 relates to rotors having cells positioned on the periphery of the rotor. Each cell includes a peripheral orifice for removing fluid introduced into the cell. U.S. Pat. No. 4,902,479 discloses a multi-cuvette rotor comprising elongated, radially extending cuvettes. Each elongated cuvette comprises a first chamber for receiving a first constituent and a second chamber for receiving a second constituent. A divider structure between the first and second chambers prevents mixing of the constituents before a predetermined time. Mixing occurs as the rotor is spun at a significant speed. U.S. Pat. No. 4,963,498 discloses devices relying on capillaries, chambers, and orifices to pump and mix fluids for optical analysis. U.S. Pat. No. 5,077,013 discloses rotors comprising peripheral cuvettes connected to holding chambers positioned radially inward from the cuvettes. U.S. Pat. No. 4,898,832 describes a rotor, which includes dried reagents adsorbed or bound to a solid carrier. A sample solution is moved along the rotor by use of centrifugal force and/or pressure force. U.S. Pat. No. 3,829,223 discloses a rotor adapted for mixing sample and reagent for photometric analysis in the rotor. Ramp-like projections on the walls of the test wells assist with mixing. U.S. Pat. No. 3,795,451 teaches a rotor for mixing a sample and reagent using a variation in rotational speed to provide mixing. A capillary passage is fed at increased rotational speeds to transfer the liquid as flow over a steep angle is permitted. U.S. Pat. No. 3,873,217 describes a rotor for photometric analysis using static loading of a main cavity and distribution of liquid to cuvettes using dynamic loading caused by rotational forces. U.S. Pat. No. 4,387,164 relates to chemical analyses of assay mediums and describes using reagents dispersed in soluble film. U.S. Pat. No. 3,881,827 teaches an apparatus and chamber for measuring cardiac output and includes a chamber for mixing a precise amount of dye with blood. U.S. Pat. No. 4,225,558 discloses a fluid test apparatus for multiple fluid samples. A sample and reagent are held in separate chambers until centrifugal force provides migration of the two fluids to a common chamber. U.S. Pat. No. 3,864,089 describes a rotor for blood fractionation. U.S. Pat. No. 4,509,856 is directed to a rotor useful for photometric analysis of a sample. U.S. Pat. No. 4,515,889 relates to the rotor having a plurality of interconnected small hollow spaces adapted for mixing reaction components. U.S. Pat. No. 4,689,203 relates to a centrifugal rotor designed for separating blood plasma from red and white blood cells. Although these inventions teach methods of combining, mixing and/or filtering samples and reagents in a rotary device, they do not allow automatic quantitative combination of reagent and sample in the device. The devices further do not provide precisely timed incubation of precisely combined reaction components before reaction products are transferred for detection.

For these reasons, it would be desirable to provide improved centrifugal rotors and methods suitable for quickly and easily mixing a volume of fluid with a reagent, and for transferring the resulting mixture from its mixing vessel to another chamber. It would be useful to transfer fluids into chambers suitable for separation of cellular components and ultimately distributed into test wells for analysis within the rotor.

U.S. Pat. No. 4,894,204 and U.S. Pat. No. 5,160,702 attempt to address some of these issues, but fail to provide high levels of reaction precision for large numbers of samples. Moreover, the complexity of design is problematic from a manufacturing standpoint. For example, the '702 patent discloses siphons for transferring fluids between chambers in a rotor. Calibration vessels have feed channels communicating with a central sample chamber and an exit orifice located in the wall opposite the feed channel. Although the siphon structures can meter somewhat controlled volumes, the precision is not high. Moreover, reaction timing and uniformity is compromised by the reaction chamber exit orifice designed to allow reaction product to escape while new fluids continue to enter. For higher precision, lower reagent and sample volumes and higher reproducibility, better fluid metering techniques would provide benefits.

U.S. Pat. No. 4,279,862 to Bretardiere is directed to a rotor, which has means for creating a pressure differential and/or turbulence to produce a homogeneous mixture of reagent and sample. Many assays can be preformed on the same assay rotor. However, sample and reagent volume precision requires manual pipetting of solutions into the device. Multistage reaction and detection schemes can not be run because reaction and detection must occur in the same chamber.

In view of the above, a need exists for analysis rotors able to accommodate relatively large numbers of test wells or cuvettes, and the rotor design should be simple and amenable to low-cost manufacture. It would be particularly desirable if the rotors were of unitary construction with no separable or movable parts. Liquid mixing methods should be simple and performable in relatively short times. Preferably, the assay methods should require relatively few steps and minimal human intervention. It would be advantageous if the methods required only rotation of the rotor in order to effect mixing and delivery of the fluid, e.g., at two or more chambers at different times. The present invention provides these and other features that will be apparent upon review of the following.

SUMMARY OF THE INVENTION

The present inventions are directed to methods and devices that provide precise timing of accurate fluid volume flows for samples and/or reagents. The flows can take place in two or more steps (e.g., initiated at different rotor speeds) so that reagent addition, filtering, reaction, detection and/or wash steps can take place at different times in an assay sequence.

The present invention provides, e.g., centrifugal fluid analyzing rotors comprising a liquid metering tube for measuring precise amounts of liquid, typically a biological sample such as plasma or whole blood. The measured sample aliquot is typically mixed with a pre-packaged reagent. The amount of pre-packaged reagent is known, and thus a precise and repeatable mixing ratio of biological sample fluid and reagent is provided.

The centrifugal assay rotor can have a plurality of assay analyzing units arranged on the same disk. Each analyzing unit can share a common sample chamber or have separate sample chambers, depending on the application needs. Each analyzing unit can also have a reagent chamber, a liquid metering tube, a mixing chamber, a mixing maze, a detection chamber and/or a waste chamber. The reagent can be pre-packaged on the rotor. As the rotor is spinning at a first speed (S1), the sample fluid can flow to fill a liquid metering tube. Optionally, S1 can be 0 rpm. Rotation speeds (e.g., S1 to S4) can be set values, or determined in real time for each assay. When the liquid metering tube is filled up, the rotor can be accelerated to second speed (S2). This can drive any sample fluid excess into the waste chamber. Meanwhile, the biological sample fluid can be held in the liquid metering tube by surface tension at a meniscus formed at the tip section (capillary port) of liquid metering tube. At this point, precise amounts of sample and reagent can be positioned in separate chambers of the device.

Next, the rotor can be accelerated to third speed (S3) to drive the reagent out of the reagent chamber into a reaction (mixing) chamber to come into contact with the sample meniscus. When the reagent meets with the meniscus of biological sample fluid held in the liquid metering tube, the retaining surface tension is lost and sample flows into the reagent to form a reaction mixture. Mixing can be enhanced by provision of mixing contours in the flow path of the fluids. Spinning at S3 can optionally generate enough force to drive the reaction mixture from the reaction chamber to a detection chamber. Optionally, the rotor can be spun at a higher speed (S4) to drive the reaction mixture from the reaction chamber into a detection chamber, e.g., after a desired reaction incubation time.

The amount of biological sample fluid released from the liquid metering tube on contact of the reagent fluid with the sample meniscus can be determined by the capillarity at the meniscus, the physical dimensions and shape of liquid metering tube, the orientation of the metering tube within the rotor, the presence or absence of additional driving forces, and surface properties of liquid metering tube. The volume of sample released can be calculated or calibrated through experiments. Since the volume of pre-packaged reagent can be precisely known, the exact mixing ratio of biological sample fluid to reagent can be controlled.

Although the chambers and channels of the analyzing units can be laid out in any number of orientations within the rotors, it is preferred that assay analyzing units be laid out generally horizontally or vertically. In units laid out horizontally, the sample chamber, reagent chamber, mixing chamber and detection chamber can all be arranged in the same horizontal plane perpendicular to a rotor vertical axis of rotation. The liquid metering tube can also lie in this plane. Alternately, features of the assay system can be arranged vertically, e.g., with the sample chamber and reagent chamber arranged in different horizontal levels of the rotor, with the liquid metering tube arranged vertically connecting those two different levels. For example, the axis of rotation of the rotor can be parallel to a vertical line connecting the sample chamber and reagent chamber. In less typical embodiments, the rotor axis of rotation is not vertical (e.g., horizontal or at least 20 degrees from vertical). In such a case, the chambers and channels will rise and fall while the rotor spins, e.g., to enhance mixing or to force a fluid through a port.

In a particular aspect of many devices, a fluid analysis rotor includes a rotational axis, a sample chamber in fluid contact with a mixing chamber through a metering tube and in fluid contact with a waste chamber through a sample waste channel, and a capillary port between the metering tube and the mixing chamber. The rotor can be configured so that at a first rotor rotation speed a liquid sample fills the metering tube but is retained from flowing into the mixing chamber by a meniscus (surface tension) of the liquid sample at the capillary port, meanwhile, liquid sample not filling the metering tube flows through the waste channel into the waste chamber at the first rotational speed. Thus, the sample fluid volume is defined by the dimensions of the metering tube between the capillary port and the flushed waste channel.

In further embodiments, a fluid analysis rotor of the invention can include, e.g., a rotational axis, a reagent chamber in fluid contact with a mixing chamber through a reagent conduit, and a sample chamber in fluid contact with the mixing chamber through a metering tube comprising a capillary port. The rotor can be configured so that when the rotor is not rotating about the axis, a liquid reagent in the reagent chamber does not flow into the mixing chamber through the reagent conduit, and liquid sample in the sample chamber does not flow into the mixing chamber through the sample capillary port (but may flow to fill the metering tube, e.g., by capillary action). The rotor can be designed so that at a first rotor rotation speed, the liquid sample fills metering tube but is retained from flowing into the mixing chamber by a meniscus of the liquid sample at the capillary port, but at a second rotor rotation speed faster than the first rotation speed, the liquid reagent flows to contact the sample meniscus in the mixing chamber. When the reagent contacts the sample, the surface tension of the sample meniscus is broken and the sample consistently flows from the metering tube to mix with the reagent in the mixing chamber. In preferred embodiments, the rotor rotational axis can be a substantially vertical axis (from a gravitational frame of reference).

In many embodiments, the metering tube is designed to have fluid flows more influenced by forces of capillarity than centripetal forces or gravitational forces. In preferred embodiments, the metering tube capillary port is configured to comprise a higher capillarity than a capillarity of the mixing chamber. In preferred embodiments, the metering tube is arranged in the rotor to have a longest dimension substantially perpendicular to a radial line from the rotational axis. That is, e.g., the metering tube is often arranged horizontally running in an arc a substantially constant distance from a vertical axis of rotor rotation. Alternately, the metering tube can be arranged to run substantially parallel to the rotor rotational axis. In embodiments where more influence of centripetal force is desired, the metering tube can run through a course that changes distance from the rotational axis.

In order to facilitate flushing excess sample fluid through the sample channel, and on to waste, a waste channel segment of the sample channel (running between the sample chamber and waste chamber, but intersecting the afferent end of the metering tube) can be substantially parallel to a radial line perpendicular to the rotational axis, and the waste chamber can be located further from the rotational axis than the capillary port is from the rotational axis. In order to prevent return of waste from the waste chamber to the sample channel, the waste channel can include a stop valve comprising less capillarity than an adjacent portion of the waste channel.

In many embodiments, the reagent chamber is located closer to the rotational axis of the rotor than the metering tube capillary port is from the axis. For example, the reagent chamber can be closer to the rotational axis than any part of the metering tube is to the rotational axis. To ensure reagent will enter the mixing chamber before the sample, the reagent conduit can include a reagent capillary port providing less capillarity (e.g., a smaller contact angle, less hydrophobic surface, and/or greater cross-sectional dimension) than the sample capillary port. Further, the reagent conduit can include a stop valve between the reagent chamber and mixing chamber, so that sample/reagent mixture can not exit the mixing chamber into the reagent chamber.

In many embodiments of the rotors, the sample is filled into the metering tube while the rotor is spinning at a first speed (S1—filling speed) and the reagent is forced to enter the mixing chamber at a second, faster, rotational speed (S2—mixing speed). In some embodiments, sample fluid flows to fill the metering tube when the rotor is not moving (S1=0 rpm), or moving only very slowly. In many embodiments, filling of the metering tube is contributed to, at least in part by centripetal force from the rotor turning at least 5 rpm, 30 rpm, 120 rpm, 1000 rpm, or more. In most embodiments, the rotor is configured to force reagent into the mixing chamber at a second rotational speed, greater than the first rotational speed. For example, the rotor can be designed to force the reagent into the mixing chamber at a rotor speed of at least 10 rpm, 100 rpm, 1000 rpm, 3000 rpm, or more.

In an aspect of the invention, the rotor can be part of a device comprising one of more detectors. Detectors can detect, e.g., fluid in the metering tube, fluid in the waste chamber, fluid in the mixing chamber, or a reaction product in a detection chamber. Detection of fluids in chambers can be used to determine when the rotor has accelerated to a speed adequate to provide a desired fluid transfer. For example, when the rotor has accelerated to a speed adequate to fill the metering tube, the rotor can be held at that speed before proceeding to the next higher speed that would cause flushing of waste into the waste chamber or mixing of reagent and sample in the mixing chamber. In this way, appropriate rotor speeds can be established in real time for analytical process steps.

Inventive methods of obtaining a sample volume using a metering tube can be practiced, e.g., using the analytical rotors of the invention. For example, a method of obtaining a sample volume in a rotary analyzer can include providing a fluid analysis rotor having a rotational axis, and a sample chamber in fluid contact with a capillary port through a metering tube and also in fluid contact with a waste chamber through a waste port at the waste chamber. It can be preferred that the capillary port be closer to the rotational axis than the waste port is to the axis. The method can further include rotating the rotor about the rotational axis at a first rotational speed, at which first speed a liquid sample from the sample chamber fills the metering tube forming a sample meniscus at the capillary port and forming a sample waste meniscus at the waste port, then rotating the rotor about the rotational axis at a waste flushing rotational speed greater that the first rotational speed, so that liquid sample pressure at the waste port is not supported by the waste port meniscus thus allowing sample to flow into the waste chamber. Meanwhile, sample pressure at the metering tube capillary port can remain stably supported by the capillary port meniscus. Thus, a volume of sample is provided in the metering tube while sample not filling the metering tube (e.g., excess sample) flows to the waste chamber. Alternately, the filling and waste flush speeds can be the same rotational speed, e.g., with metering tube filling and waste sample flushing occurring in the same step.

The methods can further include ways to precisely aliquot sample into a reagent. For example, the method can further comprise providing a mixing chamber in fluid contact with the capillary port and providing a reagent chamber in fluid contact with the mixing chamber. The rotor can be rotated at a mixing rotational speed greater than the filling and/or flushing speed, so that a liquid reagent is forced to flow from the reagent chamber into the mixing chamber to contact the sample meniscus at the capillary port. The timing of the rotor speed change can control the timing of the reagent flow and consequential mixing with sample.

The flow of reagent can trigger the flow of metered sample. For example, flow of sample into reagent can be controlled by reagent contact with a sample meniscus. A method of mixing a sample and a reagent in a rotary analyzer can include providing a fluid analysis rotor of the invention comprising a rotational axis, a reagent chamber containing a liquid reagent and in fluid contact with a mixing chamber through a reagent conduit (channel), a sample chamber containing a liquid sample and in fluid contact with the mixing chamber at metering capillary port through a metering tube. The rotor is rotated about the axis at a first rotor rotation speed where the liquid sample fills the metering tube, but does not flow past a stable liquid sample meniscus at the metering tube capillary port. The rotor is then rotated about the axis at a second rotor rotation speed faster than the first rotation speed, so that the liquid reagent flows into the mixing chamber and contacts the liquid sample meniscus. On contact, the sample meniscus is disrupted so that liquid sample is allowed to flow from the metering tube to mix with the liquid reagent in the mixing chamber.

In many preferred embodiments of the devices and methods, the sample fluid or other fluid is filtered. For example, the inventions can further comprise providing a filter in the sample chamber or in a channel of the rotor.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a conduit" can include a combination of two or more conduits; reference to "a reagent" can include mixtures of reagents, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

Descriptions used to identify relative positions of device components are generally with reference to commonly understood directions for a device on the earth, e.g., resting on a table. For example, a "vertical" axis can be described by a line running through the device to the center of the earth. Horizontal is perpendicular to vertical, or generally tangential to the surface of the earth at the point where the device is resting. Of course, this is not intended to be strictly limiting. For example, a "vertical" line can be perfectly vertical, within 40 degrees of vertical, within 20 degrees, within 10 degrees, within 5 degrees or within 3 degrees of vertical.

A central axis is a line generally running through the center of an object or conduit generally parallel to the longest dimension. For example, the central axis of a rod or tube is a line running through the center of the rod or tube along the length of the rod or tube. If the rod or tube bends through an angle, the central axis can be considered a curved line maintaining a central position and running generally parallel to the immediately adjacent walls (e.g., at points in a plane perpendicular to the axis).

A "rotational axis" is as is generally understood in the art. For example a rotational axis of a spinning object is a line running through the point of rotation and perpendicular to the plane of an arc described by a point on the object as it spins.

A "capillary port" is a port between a first chamber and/or conduit and a second chamber and/or conduit, wherein the port has capillary dimensions suitable to provide a stable meniscus (e.g., a stationary meniscus supported by surface tension) for an intended fluid contacting the port from the first chamber of conduit. For example, capillary dimensions for many aqueous solutions can be an orifice having at least one dimension ranging less than 1 mm, less than 0.5 mm, less than 0.2 mm, less than 0.1 mm, less than 0.05 mm, or less than 0.01 mm. For the purposes of this invention, the term "capillary action" will be understood to mean fluid flow due to the fluid wetting a partially or completely wettable surface. Capillary flow can be independent of gravitational force, rotational motion or centripetal force applied to a fluid on a rotor or platform of the invention.

A "sample" is typically a solution or suspension containing an analyte of interest to be detected in an assay. A liquid "reagent" is a solution or suspension that takes part in the assay to detect the sample analyte. The reagent can be a diluent, but typically also includes a reactive moiety that provides a detectable product (e.g., chemical reaction product or binding product) on interaction with the analyte. Although sample fluids and reagent fluids are typically discussed herein with regard to the devices and methods of the invention, it is understood that, in many embodiments, the fluids could be generic first and second fluids (e.g., outside of biology or medical analyses) intended for precise metering and/or mixing.

A "meniscus" is a concave surface of a liquid resulting from surface tension, typically at an interface between the liquid and a gas.

The term "about", as used herein, indicates the value of a given quantity can include quantities ranging within 10% of the stated value, or optionally within 5% of the value, or in some embodiments within 1% of the value.

DETAILED DESCRIPTION

Figure 1:
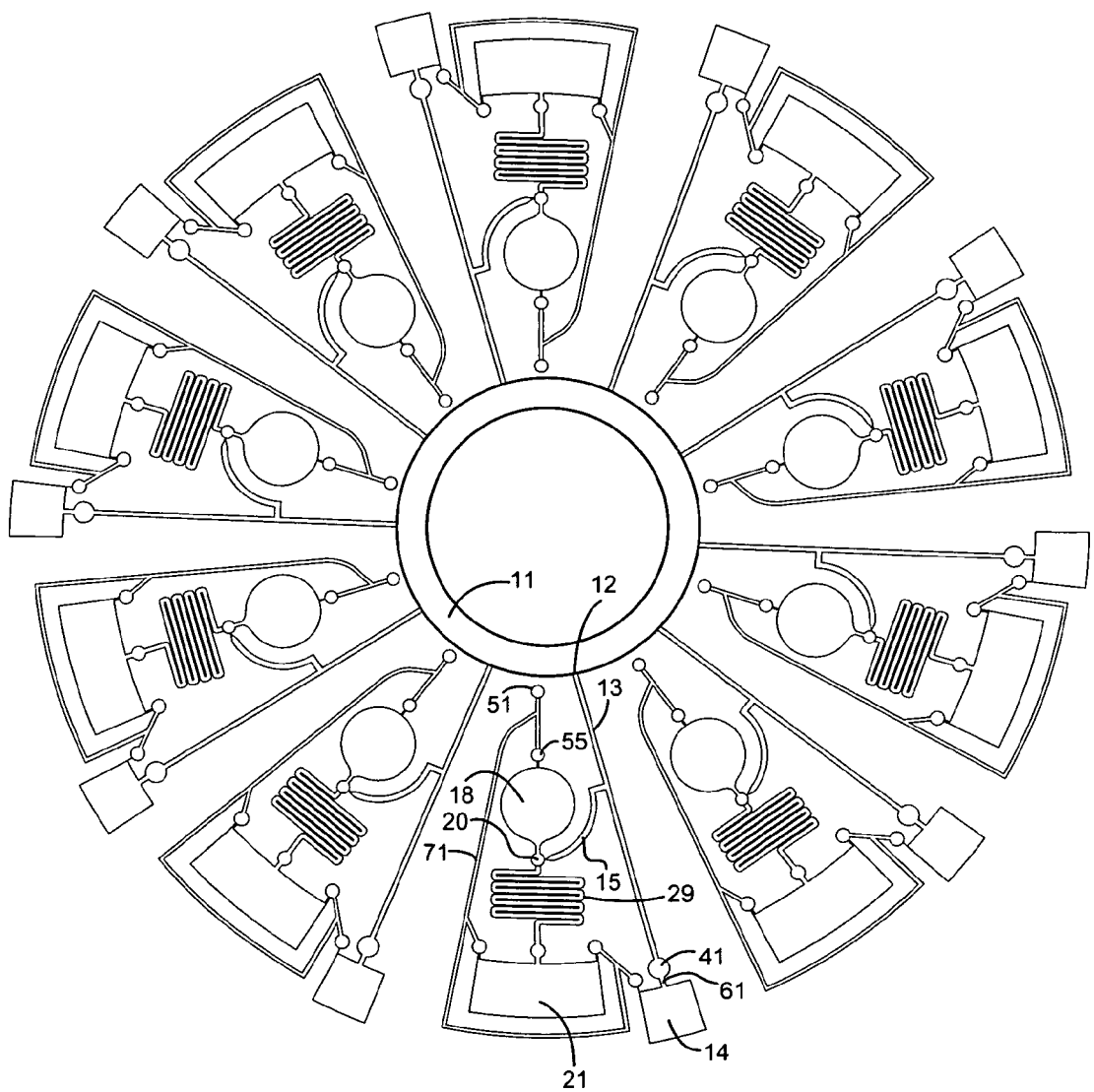
FIG. 1 is a schematic diagram of a centrifugal fluid analyzing rotor viewed looking down through the rotational axis of one preferred embodiment configured for multiple assays of a single sample aliquot on a single rotor.

The present inventions generally include methods of automatically metering precise amounts of sample through an interplay between calibrated volumes, capillary stopping forces and centrifugal driving forces. The methods can be carried out, e.g., in rotary analyzer systems comprising a volumetric metering tube containing a sample fluid between a waste channel intersection and a capillary port meniscus at a mixing chamber, and comprising a reagent chamber with a reagent channel to the mixing chamber. The components are often configured so that the reagent enters the mixing chamber at a rotation speed at which the sample meniscus remains stable. Flowing reagent can then contact the sample meniscus to release the precise amount of sample into the mixing chamber.

Microfluidic systems are often closed interconnected networks/systems of channels and reservoirs with characteristic dimensions ranging from microns to millimeters. By introducing fluids, reagents and samples into the devices, chemical and biological assays can be carried out in an integrated and automated way. In a conventional assay, two or more fluids are mixed and incubated within a microfluidic device and during, or after, this incubation period, a reaction product may be detected. It is typically the case that this microfluidic device, specifically the depths, cross-sectional dimensions, connectivity and layout of the microfluidic systems, defines the relative volumes of these fluids.

A problem in the art is that microfluidic devices, once fabricated, do not allow the user to redefine the relative volumes of the fluids to be mixed. An additional problem in the art concerns the degree and efficiency of mixing. Because the flow within a microfluidic device is laminar, mixing usually has to be brought about through mass diffusion. A typical mixing device consists of a long capillary. Two or more fluids may enter this capillary as separate fluids and leave as a single fluid. The degree of mixing can be enhanced and the time to mix these fluids can be decreased by decreasing the cross-sectional dimension of the capillary and by increasing the length of the capillary channel, but such a device can occupy a fair amount of space within a microfluidic system.

The present invention provides a microfluidic device that is conceived from a different perspective. According to one preferred embodiment of the invention, the microfluidic device has a liquid metering tube that is capable of measuring the precise amount of sample fluid to be mixed with a reagent fluid. The liquid metering is achieved, e.g., by combining flow control by centrifugal force and capillary action on a sample fluid in a microfluidic channel. In a related aspect, release of the metered sample fluid can be triggered by contact with a flow of pre-measured reagent. The mixed reagent and sample can be detected in the mixing chamber, or can controllably flow down stream to additional chambers for sequential reaction, washing and/or detection assay steps.

Rotary Devices for Precisely Metering Fluids

The devices for metering fluids generally include a metering tube precisely filled by halting (preventing) fluid flow at a capillary stop port at one end and stripping excess fluid at the other end by forcing it on to a waste chamber. The flow of the volumetrically metered fluid can be initiated past the capillary stop port by contacting the capillary stop meniscus with another fluid, e.g., causing the fluids to mix in precise proportions.

In a typical embodiment, the first fluid is a sample comprising an analyte for analysis and the second fluid is a reagent for reaction or dilution of the sample. The sample can be filled into the metering tube, e.g., by gravity, capillary action, hydrostatic pressure, and/or centripetal force. The reagent can be unmeasured, a previously measured aliquot, or can be metered in the same fashion as described for the sample. The reagent and sample capillary stop ports can empty into a common mixing chamber that can optionally also act as a reaction chamber and/or detection chamber. Alternately, forces (e.g., centripetal forces) can drive the mixture to a separate reaction chamber and/or separate detection chamber. Depending on the mechanism of the assay, detection can be by any appropriate mode, such as, e.g., photometric, galvimetric, fluorometric, physical, electronic, and/or the like.

Rotors

In typical embodiments of the devices, important driving and timing forces are provided by controlled spinning of a rotor. The basic foundation of the inventive devices is a rotor that comprises the chambers and conduits of a functioning metering and/or mixing system. Rotors are typically driven by a motor to spin about an axis. The rotor can be a substantially planar structure (e.g., disk shaped), preferably with the center of mass at the axis of rotation, and with the structural plane perpendicular to the axis. Alternately, the rotor can be a more 3-dimensional structure with substantial depth along the axis.

The rotor can be housed in a frame and powered by a motor to spin on its rotational axis. The motor can be an electric motor, hydraulic motor, air motor, turbine, and/or the like. The rotor is typically housed in the frame so as to allow access for required sample application, reagent application and/or interrogation by selected analytical product detection devices. The rotor can be driven to spin at a rotational speed ranging from about 15,000 rpm to 0 rpm, from 7,000 rpm to about 1 rpm, from 3,000 rpm to 5 rpm, from 1,000 rpm to 100 rpm, or about 500 rpm. In preferred embodiments, the speed of the rotor can be adjustable and precisely controllable.

The rotors can have any dimension, e.g., suitable for the scale of required fluid flows and/or the number of separate assays desired. Planar design rotors of the invention typically range in radius from the rotational axis from more than about 15 cm to 0.5 cm, from 10 cm to 1 cm, from 5 cm to 1.5 cm or about 2 cm. The thickness of the rotors are typically from 2 cm to 0.1 cm, from 1 cm to 0.15 cm, from 0.5 cm to 0.2 cm or about 0.25 cm. In planar rotors, the device channels, particularly the metering tube, are typically laid out substantially in a horizontal plane, e.g., perpendicular to the rotational axis. In alternate embodiments, wherein one or more channels, particularly the metering tube, are laid out with a substantially or significantly vertical orientation, the rotor can have a more substantial depth dimension (parallel to the rotational axis).

Chambers and Channels

The rotors house the chambers and channels (conduits) through which fluids can precisely and controllably flow. In a typical arrangement, there are one or more radially aligned (i.e., directed substantially along a radial perpendicular to the rotational axis) sample channels and reagent channels, in fluid contact with each other in pairs through a metering tube. Sample channels typically run from a sample chamber nearer to the rotational axis, to a waste chamber further from the axis. Reagent channels typically run from a reagent chamber nearer to the axis, to a mixing chamber, detection chamber and/or waste chamber further from the axis.

Sample channels are arranged so that sample fluid will flow from the sample chamber to fill the metering tube. In preferred embodiments, the sample channel is also in fluid contact with a waste chamber (through a waste channel section of the sample channel) and configured so there is enough resistance to waste flow to cause a back pressure, ensuring the metering tube is properly filled. In preferred embodiments, the back pressure during filling of the metering tube is not so great as to overcome the stopping force of meniscus surface tension at the capillary port where the metering tube intersects a mixing chamber. For example, assuming the sample channel enters a waste chamber through a waste capillarity port at a point the same distance from the rotational axis as the metering tube capillary port intersects the mixing chamber, the waste capillarity port can have slightly less capillarity than the metering tube capillary port, so that waste sample will flow into the waste before metered sample flows into the mixing chamber. In another example, wherein the sample channel enters a waste chamber through a waste capillarity port at a point further from the rotational axis than the metering tube capillary port intersects the mixing chamber, the waste capillarity port can have higher capillarity than the metering tube capillary port due to the additional centripetal force experienced at the waste port. That is, with the waste port further from the axis than the meter port, greater capillarity at the waste port can allow the metering tube to fill without spilling, but excess sample will break the meniscus at the waste port first with increased rotational speed, e.g., because the centripetal force is greater at a greater radial distance. It is worth noting that where capillarity is strong along the metering tube, less back pressure may be required in the sample channel to fill the metering tube.

Metering tubes are typically filled with sample fluids from the sample channel but hold sample from entering a mixing chamber through a capillary port under the forces experienced in the filling operation. Metering tubes can be arranged with any number of possible orientations in the rotor. Depending on the orientation, the metering tube capillary port can be configured to hold sample against the combined forces of capillarity, centripetal force, gravity and hydrostatic pressure resulting from the orientation. In preferred embodiments, the metering tube is oriented horizontally with the tube central axis running in an arc a constant distance from the rotational axis. In this way, the force of gravity and centripetal force are substantially neutralized, with metering tube filling simply controlled by capillarity and/or back pressure due to resistance to sample flow through the sample channel to waste. Alternately, the metering tube can have the capillary port somewhat further from the rotational axis than the tube end intersecting the sample channel; in this way, filling can be enhanced and metered sample can be more thoroughly expelled into the mixing chamber by centripetal force. In further alternate embodiments, the metering tube can be oriented with a substantial vertical dimension, e.g., to allow gravity to aid in filling and expelling sample.

Reagent channels run from a reagent chamber to a mixing chamber and, typically, on to a detection chamber. In most cases, the reagent chamber is closer to the rotational axis than the metering tube capillary port is to the axis so that reagent can conveniently run toward the sample capillary port under the influence of centripetal force. In preferred embodiments, there is a reagent capillarity port between the reagent chamber and the mixing chamber. In embodiments wherein the reagent capillary port is the same distance from the rotational axis as the metering tube capillarity port is to the axis, the reagent capillarity port can be configured to have less capillarity than the tube port, so the reagent meniscus will be broken at a lower rotational speed than the tube meniscus (of course, the selected capillarity should be further adjusted for other considerations, such as, e.g., the relative hydrostatic head pressures between the metering tube and reagent chamber, etc.). In preferred embodiments, wherein the reagent enters the mixing chamber at a point closer to the axis than does the metered sample, the reagent capillarity port can have a relatively lower capillarity (also taking into account the relative head pressures).

The mixing chamber is, e.g., the chamber in which reagent and sample fluids first come into contact. Depending on the complexity of the selected analysis, the mixing chamber can have multiple functions including, e.g., mixture of reagent and sample, dilution, incubation, washing, and/or detection. In most embodiments of the invention, the mixing chamber functions only in timing of mixing and incubation of reactions. In preferred embodiments, the mixing chamber has a reagent entry port closer to the rotational axis than the metering tube capillarity port is to the axis. In this way, flow of the reagent from the reagent chamber can be forced to flow into contact with a meniscus of sample retaining sample at the capillarity port. The mixing chamber can have contours and dimensions that enhance or control mixing and incubation. For example, the chamber can include particles or surfaces that increase turbulence in the fluid flows, the chamber can be thermostatically controlled, the chamber can include a conduit (e.g., a mixing maze) that influences mixing and incubation time. The mixing chamber can include an exit port located radially outward so that the reagent/sample mixture can flow under centripetal force to another chamber, such as a chamber specialized for reaction, washing, detection, and/or receiving waste.

Many embodiments of the rotor include a detection chamber. After sample has mixed with a reagent (or conditioning buffer diluent) it can pass from the mixing chamber to the detection chamber where the product of an analyte of interest and a reagent can be detected in an appropriate manner. For example, in many embodiments, the detection chamber includes one or more transparent walls so that a reaction product can be interrogated with a light source for detection of reaction product, e.g., by absorbance or fluorescence. In other embodiments, the detection chamber can include a surface having affinity molecules to capture a reaction product or analyte of interest; unbound materials can be washed out of the detection chamber; and, bound materials detected as appropriate for the selected assay method.

The channels and chambers of the device can have dimensions appropriate to, e.g., the assay method, sample size, flow forces and rotor size desired. The chambers of the device typically range in volume from more than about 10 ml to 1 ml or less, or less than 0.1 ml, less than 0.01 ml or 0.01 ml or less. The channels range in length from more than about 100 cm to 10 cm or less, or less than 1 cm, less than 0.1 cm, or less. The internal diameter of the channels can range, e.g., from more than 5 mm to 1 mm or less, or less than 0.1 mm, 0.01 mm, or less.

Chambers and/or channels can be transparent or include detection surfaces (e.g., electrodes) allowing detection of fluid within. In this way, proper rotor speeds can be detected in real time for fluid transfers described herein.

Other Device Components

Other device components can be included in the analytical rotors of the invention to provide special features or additional flow control. For example, the devices can include filters, stop valves, and/or vents.

Filters can be included in the device to, e.g., stably hold fluids, remove particles (e.g., blood cells) from samples, and/or to prevent clogging of the channels and ports. The filters can be any appropriate type, such as, e.g., a mesh, packed particles, a fibrous matt, a porous matrix, and/or the like. In one embodiment, a filter is mounted in the sample chamber, or between the sample chamber and the metering tube to remove over-sized particles from the sample.

Stop valves are one-way valves that prevent reverse flow of fluids in the channels of the device. Stop valves can provide a back pressure, as desired due to surface tension at a port. Stop valves can be any appropriate valve such as a ball valve, solenoid valve, needle valve or reed valve. In a preferred embodiment, the stop valve prevents reverse flow based on capillarity. For example, a stop valve can comprise a narrow port or channel between a chamber and a "bubble" in the channel. Should a fluid enter the narrow channel from the chamber, it may flow to the bubble where surface tension (increased contact angle) of the fluid prevents further migration into the expanded cross-sectional dimensions of the bubble.

Sample fluids are much discussed above. Although sample fluids for analysis are preferred embodiments of the invention, the fluids, e.g., metered by the metering tubes of the rotors can be any fluid desired to be metered and/or mixed using the devices and/or methods of the invention. In preferred embodiments, the sample fluid is, e.g., a biological fluid, a pharmaceutical solution, a process intermediate, a chemical product, and/or the like. In a most preferred embodiment, the sample fluid is blood or a blood component, such as serum or plasma.

Reagents in the rotors can be any appropriate for the assay method selected and/or the analyte of interest. Representative reagents include, e.g., antibodies, labeled antibodies, labeled ligands, reactive chromophores, reactive fluorophores, enzymes, nucleic acids, diluents, buffers, pH indicators, and/or the like.

In addition to the sample metering tube system, rotors of the invention can include additional metering tubes to volumetrically meter reagents, e.g., in a time-controlled fashion. For example, a reagent metering tube can be established upstream (e.g., closer to the rotational axis), downstream, and/or adjacent to the sample fluid metering tube. In one embodiment, a reagent metering tube system is established with reagent channels arranged so that reagent fluid will flow from the reagent chamber to fill the reagent metering tube. The reagent channel can also be in fluid contact with a reagent waste chamber and configured so there is enough resistance to reagent waste flow to cause a back pressure ensuring the metering tube is properly filled without reagent flowing past a reagent capillarity port. The reagent capillarity stop port meniscus can hold the reagent while it fills the metering tube and as excess reagent is flushed to waste, but the meniscus can be broken at a rotor rotation speed below that which would break the sample meniscus (or by contact by another fluid, such as a diluent or other reagent). As described above, reagent released from the reagent capillarity port can contact the sample meniscus in the mixing chamber to precisely proportion and mix with the sample. In alternate embodiments, mixing can be initiated by flow of sample from a metering tube to contact the meniscus of a reagent.

Methods for Precisely Metering Fluids in Capillary Devices

The inventions include methods of obtaining a precise sample volume using a metering tube volume defined by a capillary port at one end and centrifugal flushing of excess sample at the other end. The methods can further include release of the metered sample by contacting the meniscus of the sample at the capillary port with a reagent flowing under centripetal force.

The methods can generally include providing an analysis rotor, as described above, with a metering tube closer to the rotor rotational axis than a waste port is to the axis; rotating the rotor at a speed at which a sample meniscus at the metering tube capillary port is stable, but at which speed excess sample not in the tube is forced past a waste port into a waste chamber.

The methods can include methods of mixing two fluids. For example, an analytical rotor can be provided, as described above, with both a metering tube and reagent chamber in fluid contact with a mixing chamber. The method can further comprise pre-staging the rotor so that sample volume is metered in the tube with a sample meniscus at the metering tube capillary port and reagent is present in the reagent chamber. The rotor can be rotated at a speed at which the sample meniscus remains stable, but reagent flows into the mixing chamber. When the reagent contacts the sample meniscus, the sample is released from the metering tube to mix with the reagent in the mixing chamber.

Metering Sample

Sample volumes are metered in analysis rotors of the invention by flowing sample into a metering tube to a point where surface tension at a capillary port generates a stable meniscus preventing further flow, e.g., at a mixing chamber. Excess sample can be precisely stripped from the intersection of the metering tube at a sample channel, e.g., by one or more forces flushing excess sample further along the sample channel, e.g., to a waste chamber. The deliverable sample volume in the metering tube is precisely determined by the volume of the tube, precise locating of the capillary port meniscus and the precise and repeatable sample flushing at the sample channel intersection of the metering tube.

Sample fluid can be filled into the metering tube by any appropriate means. Sample can be applied to a sample chamber to flow into a sample channel and on to the afferent and efferent ends of the metering tube. Sample can flow in the sample channel under the influence of, e.g., capillary action, hydrostatic pressure, pneumatic pressure, electroosmosis, centripetal force, and/or the like.

The metering tube can be filled by capillary attraction between the sample fluid and the walls of the sample channel and/or metering tube. The rate and pressure of such flows can be influenced, as is known in the art, e.g., by the nature of the fluid, nature of the channel walls, cross section of the channels, and the like. For example, where the sample fluid is an aqueous fluid or suspension, the channel and/or tube walls can have a hydrophilic character. Where the rotor is made of hydrophobic materials, such as in many plastics, the walls can be treated with ionizing light or ionic discharges, treated with surfactants, provided with textures, derivatized with hydrophilic molecules, and the like, to enhance capillary interactions with aqueous samples. For metering and flow of hydrophobic sample fluids, capillary action can be enhanced by ensuring more hydrophobic channel surfaces. The cross-sectional dimensions of the channel and/or tube can include at least one capillary dimension to promote flow of the sample by capillarity. In some embodiments, sample can flow from the sample chamber by capillary action to fill the sample channel and/or metering tube. In some embodiments, the metering tube is filled with sample without any significant flow contribution due to centripetal force.

In preferred embodiments, sample flows to the metering tube are driven at least in part by centripetal force of rotor rotation. For example, sample can fill the metering tube by applying sample to the sample chamber, rotating the rotor at a first rotation speed generating centripetal force causing the sample fluid to flow radially into and along a sample channel to make contact with an afferent end of a metering tube. The centripetal force can cause sample fluid to flow into a waste section of the waste channel and/or into a waste chamber. In many embodiments, the centripetal force can cause sample fluid to flow into the metering tube. In one embodiment, flow in the sample channel is substantially driven by centripetal force, while sample flow into the metering tube is provided predominantly by capillary action.

The sample fluid flow into the metering tube is typically limited when the sample fluid front encounters a capillary port where a meniscus is generated with a surface tension adequate to counter the filling pressure. The methods include providing a capillary port at the efferent end of the metering tube. The capillary port can have a capillary surface, port dimension, and/or port topography, that provides adequate meniscus surface tension to stop further flow into the metering tube. For example, the capillary port can include a region of lower hydrophilicity or higher hydrophobicity, thus increasing the contact angle of aqueous sample fluids relative to other surfaces of the metering tube. The associated reduction in attraction between the sample fluid and capillary port surface can restrict flow past the surface and precisely halt flow into the metering tube. In many embodiments, a cross-sectional dimension of the metering tube can increase at the capillary port, thus physically increasing the contact angle between the fluid and the port surface, and inhibiting flow past the capillary port.

Once the metering tube is filled from the afferent end intersection with the sample channel to the capillary port, it is usually desirable to flush excess sample fluid from the intersection. In preferred embodiments, the excess fluid is replaced with a gas to create a gas/fluid interface (meniscus) at the afferent end of the metering tube. Alternately, the excess sample fluid can be flushed from the intersection with a flush liquid. In preferred embodiments, the excess fluid is flushed from the intersection by centripetal force generated by rotating the rotor. The centripetal force can fling excess fluid on to a waste channel and/or waste chamber and replace the fluid with gas (typically air vented from the sample chamber). In other embodiments, the excess sample fluid can be flushed by a pressurized gas.

Mixing Two Fluids with Precision

Methods can provide a mixing chamber having a port of entry for reagents from one or more reagent chambers, and a sample capillary port of entry of a metered sample fluid. The metered sample and/or reagent can be forced into the mixing chamber by any suitable force, such as capillary action, a pressure differential, gravity and/or centripetal force. In a most preferred embodiment, the reagent is forced into the mixing chamber by centripetal force. Once in the mixing chamber the reagent fluid can contact a meniscus of sample fluid at the metering tube capillary port, thus breaking the surface tension of the meniscus. The reagent and sample can simply mix on contact and/or be actively mixed by features of the mixing chamber.

In one embodiment, a precise amount of sample fluid is mixed into a reagent within the mixing chamber. A precise amount of sample fluid can be held in the metering tube and prevented from flowing into the mixing chamber by surface tension of a meniscus at the sample capillary port. Forces acting on a reagent can cause it to flow into the mixing chamber to contact the sample meniscus, thus breaking the surface tension and allowing the metered sample to flow in response to forces acting on it. For example, before mixing, the rotor can be spinning at a first rotational speed (e.g., a filling and/or flushing speed at which excess sample fluid was flushed from the sample channel to waste) with the sample fluid held at the capillary port meniscus and with reagent held in a reagent chamber by a reagent capillary port. To initiate mixing, the rotor can be spun at a higher rotational speed (mixing speed) selected to be fast enough for the reagent to overcome the surface tension of the reagent meniscus, but not fast enough for the sample fluid pressures to overcome the surface tension of the sample capillary port meniscus. The mixing chamber can be configured so that reagent fluid flowing into the mixing chamber will be directed to contact and break the sample meniscus. With the sample meniscus disrupted, the metered sample will flow (under the influence of gravity, hydrostatic and/or preferably centripetal force) to contact and mix with the reagent flow.

Admixture of fluids (e.g., reagent and sample) can be accomplished any number of ways in the mixing chamber. For example, the reagent and sample can flow together in a mixing channel of the mixing chamber, so that they eventually are adequately mixed by, e.g., passive diffusion and/or turbulent flow. In one embodiment, the mixing chamber itself has an exit channel controlled by a mixture fluid capillary port that provides a stable meniscus at the present rotational speed of the rotor. The combined reagent and sample can be held in the mixing chamber, e.g., to mix by diffusion or swirling due to rotor accelerations, until the rotor speed is further increased to the point where the mixture meniscus is overwhelmed by centripetal force. In optional embodiments, the mixing chamber can include mixing contours that enhance mixing of the sample and reagents, such as, e.g., projections, obstructions, packed particles, texturized walls, and the like.

In an embodiment, the rotational speeds for filling, mixing, transfer to detection chambers, and the like, is not preset, but is determined in real time by monitoring flows in the rotor. For example, instead of driving the rotor as a standard meter tube filling speed, the rotor can gradually accelerate until a detector (e.g., light absorbance detector or electrode) detects sample at the capillary port. In a similar fashion, mixing speed can be detected when the rotor has accelerated to a speed at which reagent is detected in the mixing chamber. The use of real time rotor speed determinations for assay process steps can provide a consistent process, e.g., even where the viscosity, hydrophilicity and/or temperature of fluids varies from run to run. Further, rotor speed control responsive to actual fluid controls can lower rotor manufacturing costs by, e.g., allowing more variability in channel surface character and dimensions.

Processing of Sample/Reagent Mixtures

In most embodiments of the methods, the sample and reagent are mixed to ultimately provide a detectable reaction product. The sample and reagent can react in the mixing chamber and the product can be detected in the mixing chamber. Alternately, the mixture can flow into a reaction chamber where the product can optionally be detected. In another alternative, the reaction product can flow from a reaction chamber to a detection chamber for detection of a product of a sample analyte reaction with a reagent. In many embodiments, the sample/reagent mixture is ultimately flushed or washed from a chamber before detection of a product.

In many embodiments, the reaction of reagents and sample analytes can be detected at the time of mixing. For example, in many calorimetric assays a chromophore reagent changes color on contact with an analyte of interest. In such as case, the new color can be immediately detected spectrophotometrically in the mixture.

In other embodiments, the mixture of reagent and sample needs time to react, e.g., at a certain temperature, for a certain time, and/or with a second reagent. The methods include the aspect of flowing the mixture into a reaction chamber to complete the assay reaction chemistries. For example, where the mixture is merely a dilution with a diluent reagent, the mixture can flow into a reaction chamber to contact a reactive reagent that provides the reaction product for detection. In some embodiments, the reaction product of the sample analyte and reagent can flow into a reaction chamber to be captured for detection. For example, an antigen analyte can mix with a fluorescent antibody reagent and flow into a reaction chamber to be captured by another antibody attached to a solid support in the reaction chamber. In this case, the reaction chamber also acts as a detection chamber wherein a light source is directed at the solid support to detect the presence of captured antigen/antibody product.

In another aspect to the invention, a wash buffer can be provided, e.g., to wash away excess assay constituents to reduce background noise in the detection. For example, a wash buffer chamber can be provided with a capillary port that holds the wash buffer until a rotor speed is reached, wherein the buffer pressure due to centripetal force overwhelms the buffer meniscus. A flow of wash buffer can be timed to rinse the reaction chamber or a detection chamber before the detection step of the analysis.

EXAMPLES

The following examples are offered to illustrate, but not to limit the claimed invention.

Example 1

General Metering by Contact of Fluids

Figure 3A:
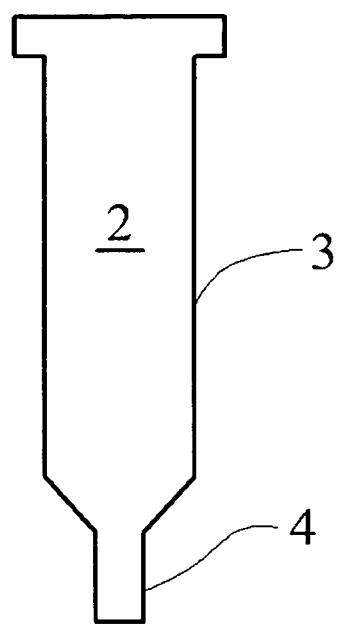
FIG. 3A schematically illustrates a pipette tube with a capillary port tip.

To illustrate the principles of liquid metering according to one preferred embodiment of present invention, we now refer to FIGS. 3A-F. In FIG. 3A, it shows a schematic of a microfluidic tube 2 which has a body section 3 and tip section 4. The tip section 4 has a relatively smaller diameter than the body section 3. The typical dimensions of the diameters of body section 3 and tip section 4 range from several microns to several hundred microns. The length of the tube 2 is on the order of several hundred micrometers to a few centimeters.

Figure 3B:
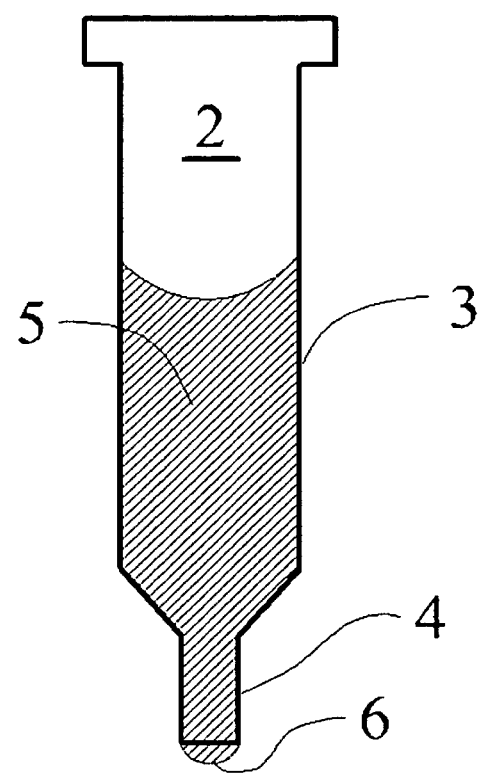
FIG. 3B schematically illustrates a sample biological fluid retained in a pipette tube by a capillary port.

Referring to FIG. 3B, a first fluid 5 is added into the said microfluidic tube 2. This first fluid 5 can be, e.g., a biological fluid, an ordinary soft drink, a chemical or even drinking water. Under the capillary force, the first fluid 5 will maintain a certain amount of volume in the microfluidic tube 2 as illustrated in this schematic. At the same time, the first fluid 5 will also form a meniscus 6 at the top of tip section 4. The surface tension force acted upon the meniscus 6 will keep the first fluid 5 in the microfluidic tube 2, and keep it from dropping out of the microfluidic tube 2.

Figure 3C:
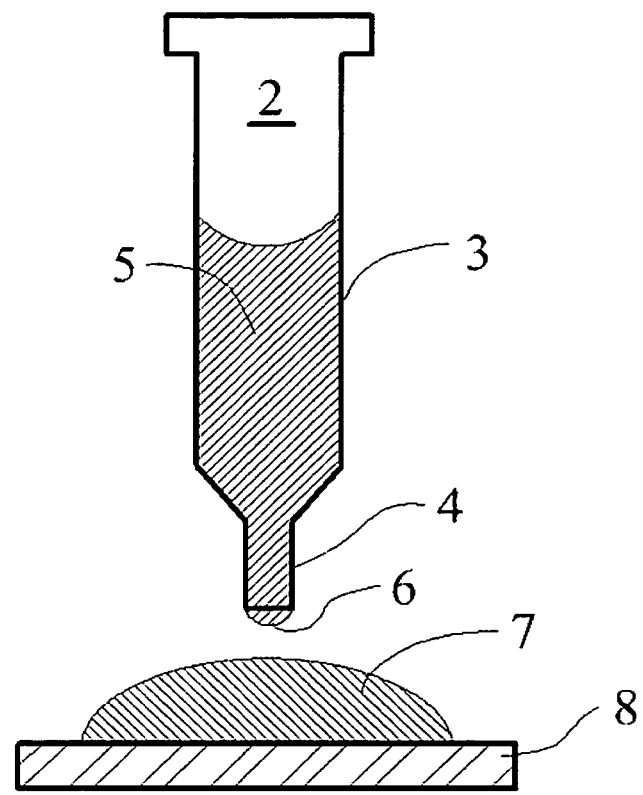
FIG. 3C schematically illustrates a sample fluid filled in a pipette tube with the capillary port proximal to a fluid resting on a flat surface.
Figure 3D:
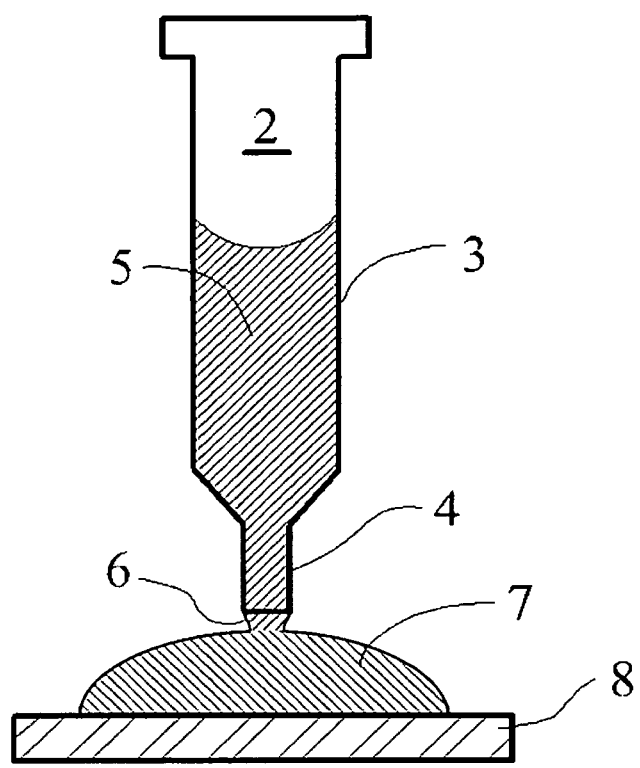
FIG. 3D schematically illustrates breaking of the capillary meniscus when the sample of fluid contacts the fluid on a flat surface.

As illustrated in FIG. 3C, a second fluid 7 is dropped to lie on a flat surface 8. This second fluid 7 can be a biological fluid, an ordinary soft drink, a reagent, a chemical or even drinking water. The second fluid 7 can be the same or different from the first fluid 5. When microfluidic tube 2 is moved close enough to contact the second biological fluid 7 on the flat surface 8, the first fluid 5 in the microfluidic tube 2 meets with the second fluid 7 on the flat surface 8, see FIG. 3D. The meniscus 6 is disrupted by breaking of the surface tension. This causes the discharge of first fluid 5 from the microfluidic tube 2, so that some amount of first fluid 5 flows into the second fluid 7. Fluid mixture 9 thus formed contains both first fluid 5 and second fluid 7.

Figure 3E:
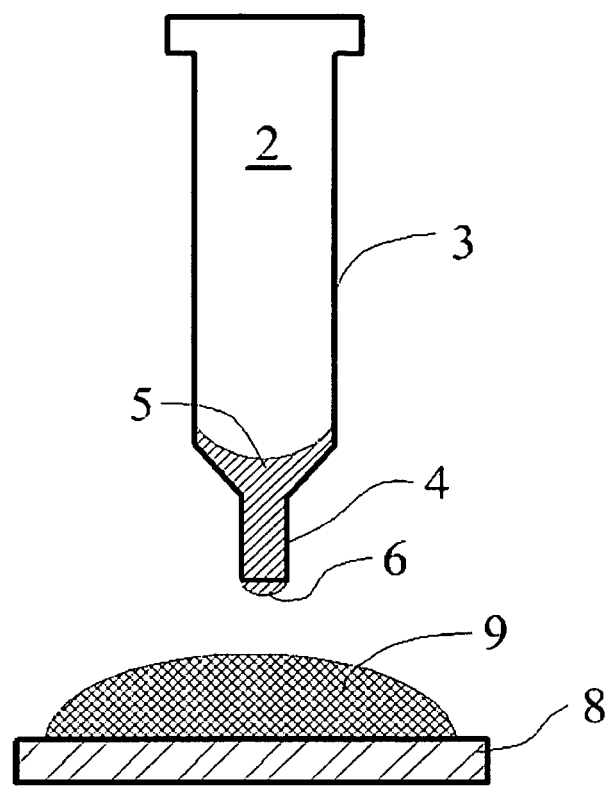
FIG. 3E schematically illustrates sample fluid mixed with the surface fluid after contact of the fluids.

When the microfluidic tube 2 disengages from the fluid mixture 9, as shown in FIG. 3E, a new meniscus 6 can then be formed at the end of tip section 4 of the microfluidic tube 2. This time, it may or may not have the same radius of curvature as that before the tube 2 makes the contact with second fluid 7.

Figure 3F:
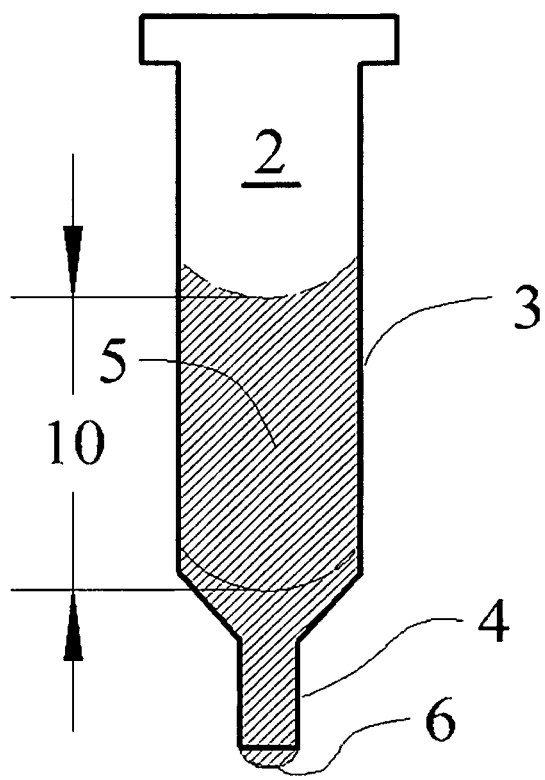
FIG. 3F schematically illustrates the calculation of a predictable and repeatable volume of sample fluid discharged from the pipette tube.

The amount of first fluid 5 added into the second fluid 7 can be calculated by looking at the fluid height difference before and after the discharging of first fluid 5 into second fluid 7. As shown in FIG. 3F, the height difference 10 multiplied by the known cross-sectional area of microfluidic tube 2 gives the volume of first fluid 5 added to the second fluid 7. As such, the microfluidic tube 2 can function as a liquid volume meter.

Example 2

Multi-Assay Rotors with a Sample Metering Tubes

A centrifugal fluid analyzer rotor incorporating a fluid contact triggered metering tube according to one preferred embodiment of present invention is shown in FIG. 1. The rotor has a plurality of assaying units, each connected to a common sample chamber 11 through sample inlet opening 12 and sample channel 13. The sample channel 13 is connected to a liquid metering tube 15, and also waste chamber 14 through bubble 41 and a narrow section 61. Narrow section 61 and the bubble 41 form a capillary stop valve such that the sample biological fluid stored in the waste chamber 14 can not flow (e.g., by capillary action) back into the sample channel 13.

Figure 2:
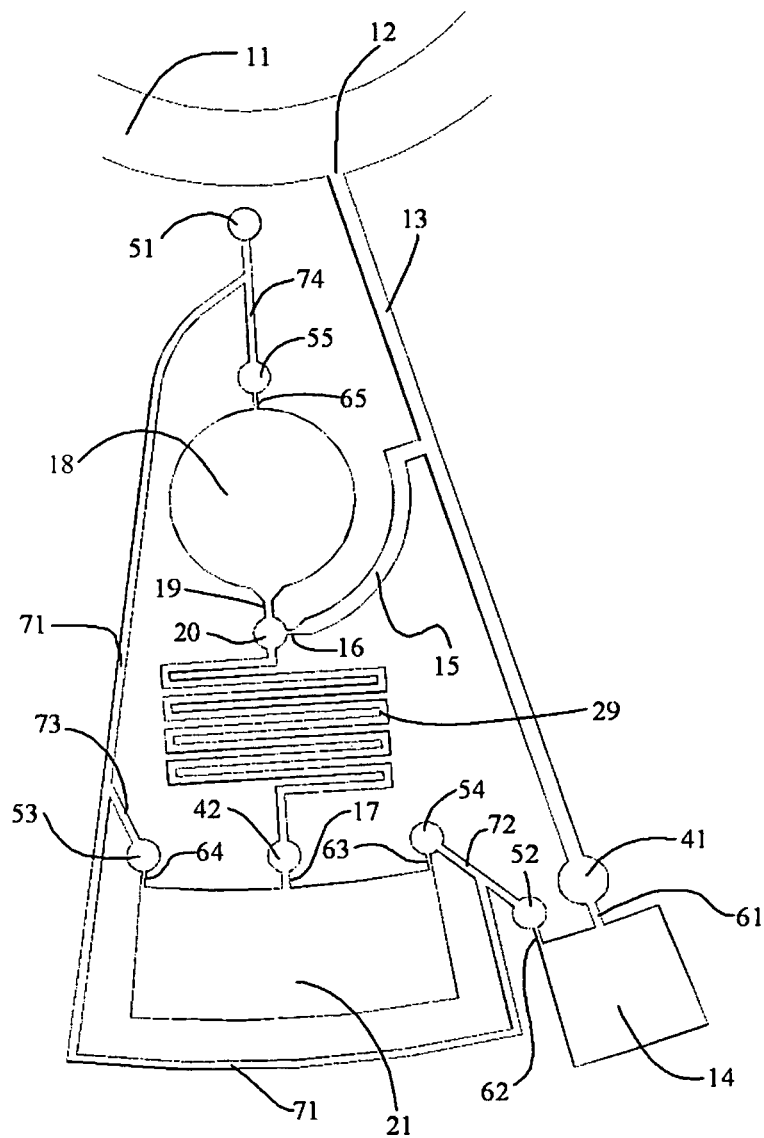
FIG. 2 shows detailed view of one assay unit of centrifugal fluid analyzing rotor wherein the reaction chamber includes an mixing/incubation maze.

A more detailed view of one assaying unit of the centrifugal fluid analyzer rotor is shown in FIG. 2. In addition to what is described earlier, this assaying unit includes reagent chamber 18, a mixing chamber 20 and a detection chamber 21. The reagent chamber 18 is connected to the mixing chamber 20 through channel 19 (reagent capillary channel). In the mixing chamber 20, an assay reagent can contact a biological fluid stored in the liquid metering tube 15 resulting in admixture of the fluids. The reaction mixture then flows through mixing maze 29 of the mixing chamber to reach bubble 42. The mixture can then flow into the detection chamber 21 through channel 17. Channel 17 can optionally have a capillarity with the reaction mixture that stops or delays flow into the detection chamber until defined conditions (e.g., rotation speed) are met. The bubble and channel 17 can form a capillary stop so that the reaction mixture, having flowed into the detection chamber 21, will not flow back through the bubble 42 to the mixing maze 29.

The reagent used for assaying is initially sealed in the reagent chamber 18. To facilitate reagent flow into the mixing/reaction chamber 20, an air ventilation bubble 51 is provided. This ventilation bubble 51 is in fluid contact with the external environment and allows air to flow into the reagent chamber 18 through channel 74, bubble 55 and narrow channel 65 when the reagent flows to mix with the biological fluid stored in the liquid metering tube 15. Again, bubble 55 and narrow channel 65 form a capillary stop valve so that reagent stored in the reagent chamber 18 does not back fill the bubble 55 and channel 74.

Bubble 51 also provides air ventilation for detection chamber 21 through channel 71 and channel 73. Similarly, bubble 51 provides air ventilation to waste chamber 14 through channels 71 and 72. Bubble 53 and channel 64 form a capillary stop valve such that the reaction mixture in the detection chamber 21 does not flow into the bubble 53 and thus the ventilation channel 73. Similarly, bubble 54 and channel 63 also form another capillary stop valve so that reaction mixture does not flow into the ventilation channel 72. Furthermore, bubble 52 and channel 62 forms yet another capillary stop valve, e.g., preventing waste from entering the detection chamber.

In general, the microchannels in the assaying unit of the centrifugal fluid analyzing rotor, according to one preferred embodiment of present invention, has diameters ranging from tens of micrometers to a few hundred micrometers. The length of each microchannel is so determined such that the assaying unit is able to accomplish the mixing and detection of biological agents.

Example 3

Precise Metering of a Sample Fluid into a Reagent

Figure 4A:
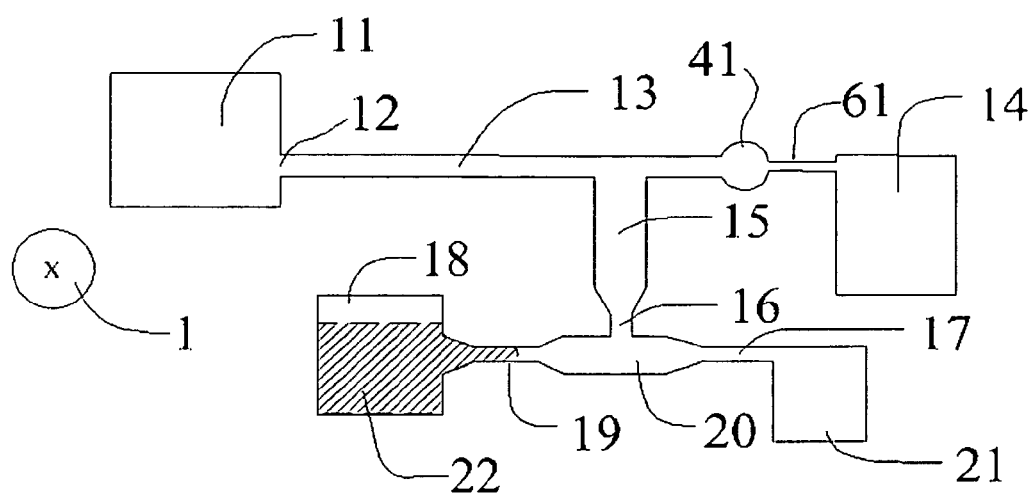
FIG. 4A is a schematic diagram showing a fluid flow system of centrifugal fluid analyzing rotor. Reagent is held in a reagent chamber at a reagent channel. Note the chambers and channels are arranged in a plane perpendicular to the axis of rotor rotation.

To understand more about the working principles of the centrifugal fluid analyzing rotor according to one preferred embodiment of present invention, we refer to FIGS. 4A-H. These figures schematics that are used to illustrate the principles, but are not intended to limit the scope of the inventions. In FIG. 4A, sample chamber 11, reagent chamber 18, liquid metering tube 15, waste chamber 14, and detection chamber 21 are all fluidly connected through a network of micro channels, e.g., similar to those shown in FIGS. 1 and 2. In reagent chamber 18, reagent 22 is pre-packaged in a known desired volume, as shown in FIG. 1. To simplify the drawings, the mixing maze 29 and bubble 42 are not drawn in the figure. In this figure, the (vertical) axis of rotation 1 is shown such that the rotation of the assay analyzing unit is in the plane as shown. In this case, FIGS. 4A to 4H show the plan view of an assay analyzing unit. The sample chamber 11 and reagent chamber 18 are arranged in the same level of plane. The liquid metering tube 15 is arranged horizontally in the same level of the rotor plane.

Figure 4B:
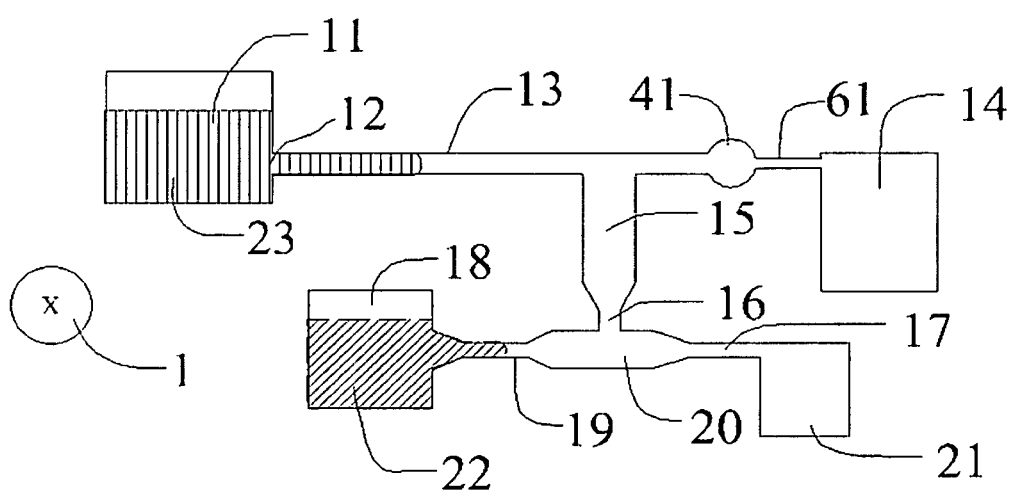
FIG. 4B shows a schematic diagram wherein a sample fluid intended for analysis has been added to a sample chamber.
Figure 4C:
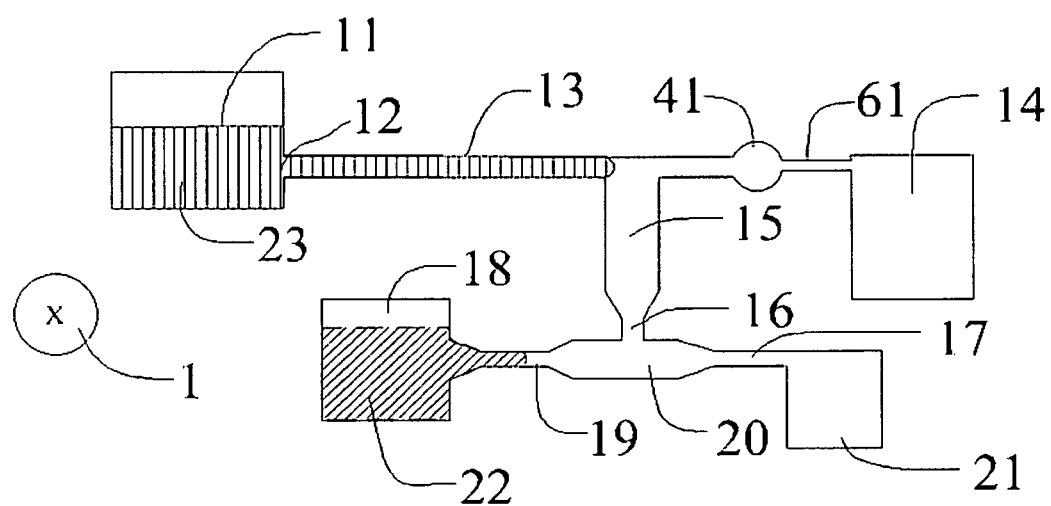
FIG. 4C shows a schematic diagram of sample fluid filling a sample channel.
Figure 4D:
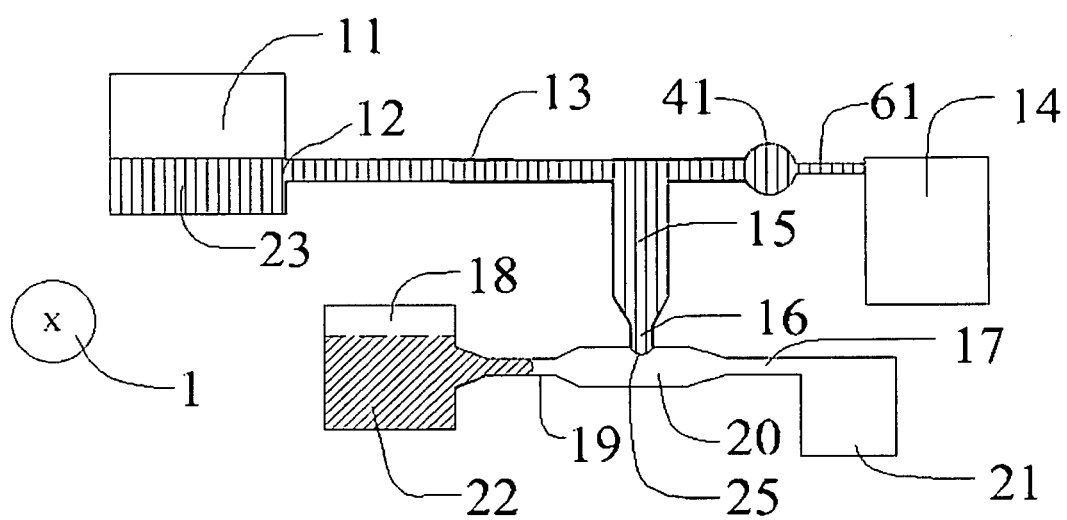
FIG. 4D shows a schematic diagram of sample fluid having filled a metering tube to the extent allowed by the metering tube capillary port.

Referring to FIG. 4B, biological sample fluid 23 has been added to the sample chamber 11. As soon as the sample fluid 23 is added into the sample chamber 11, it starts moving along the channel 13 by capillary action. But the channels are configured (e.g., by channel diameter control) so that the sample fluid stops at the intersection of channel 13 and liquid metering tube 15, as shown in FIG. 4C, due to a capillary stop force so formed at the intersection. When the rotor is spun at a speed S1, the centrifugal force overcomes the capillarity stop. At speed S1, the biological sample fluid 23 is driven to fill liquid metering tube 15 until stopped by generation of a stable meniscus 25 at capillary port 16. Bubble 41 and channel 61 are also filled with sample fluid 23 at speed S1, as shown in FIG. 4D.

Figure 4E:
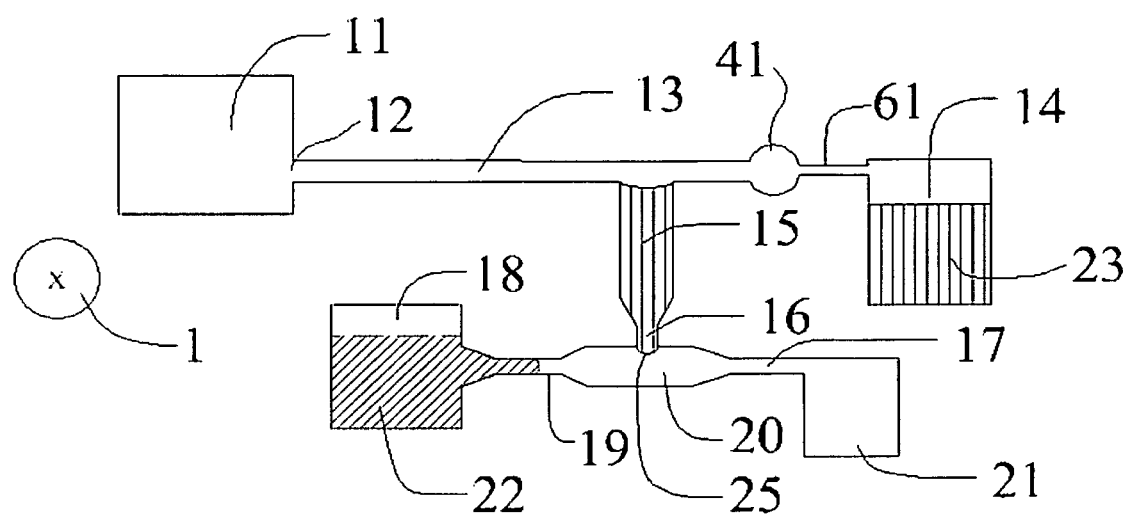
FIG. 4E shows a schematic diagram wherein excess sample fluid has been flushed to a waste chamber, leaving a precisely filled metering tube.

A second capillary stop meniscus is also formed at to the intersection of channel 61 and waste chamber 14. In order to overcome this second capillarity, the rotor is now spun at speed S2 (preestablished or determined in real time), greater than S1. At this rotational speed, the centrifugal force is enough to drive all sample fluid 23 that is originally filled in the channel 13, bubble 41 and channel 61 into waste chamber 14. This is illustrated in FIG. 4E. At the same time, the biological sample fluid 23 that was filled into the liquid metering tube 15 is not affected by the rotor spinning at the speed S2. The tip section 16 of the liquid metering tube 15 is designed to create enough capillary stop pressure to hold biological sample fluid 23 in place in the liquid metering tube 15 at spin speed S2. The liquid metering tube 15 is configured not to break the meniscus 25 at speed S2. For example, the sample meniscus at the metering tube is closer to the axis of rotation 1, thus experiencing less centripetal force than, e.g., the fluid at the second capillary stop at the waste chamber.

Figure 4F:
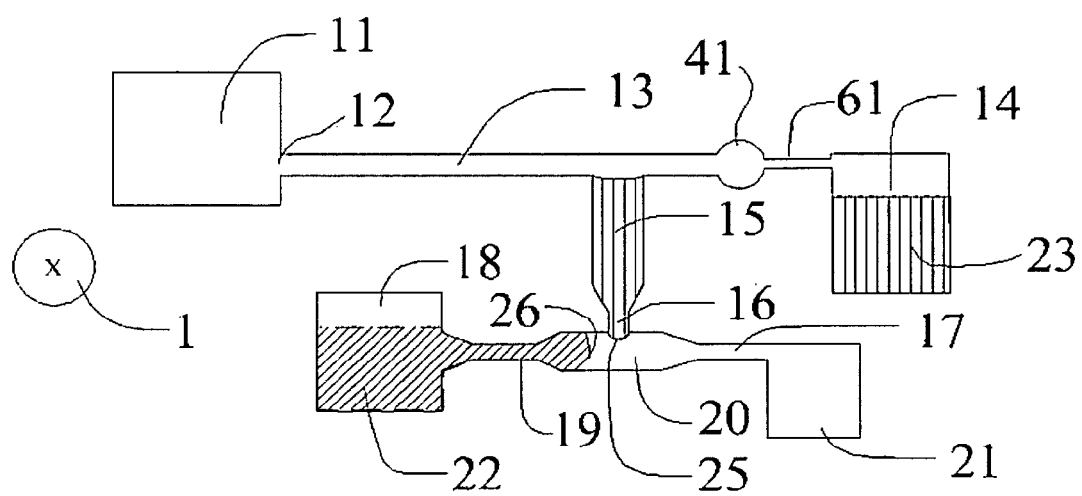
FIG. 4F shows a schematic diagram wherein reagent fluid pressure has exceeded capillarity surface tension at the reagent channel capillary port, allowing reagent to flow into the reaction chamber.
Figure 4G:
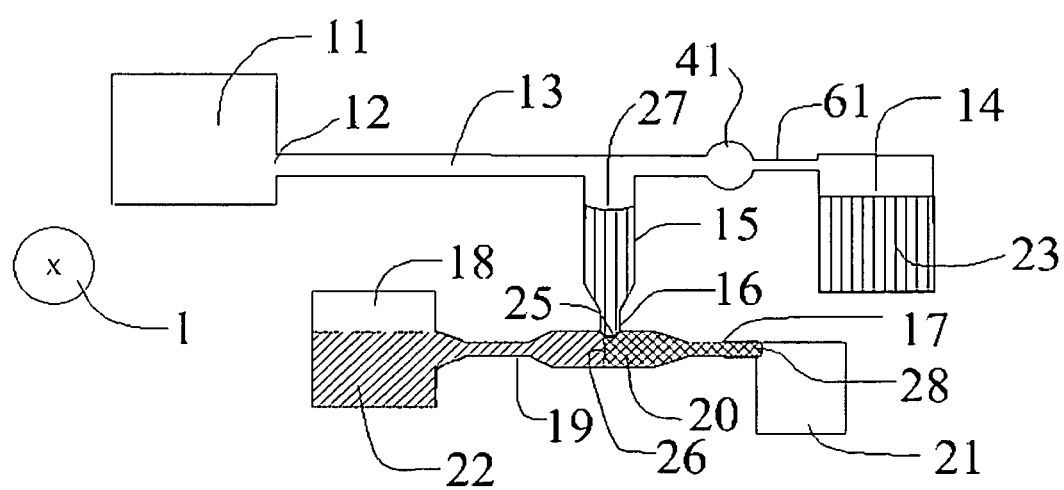
FIG. 4G shows a schematic diagram of sample mixing with reagent on contact of the reagent fluid with the sample meniscus at the metering tube capillary port.

The rotor can next spin at speed S3, which is faster than S2. This allows the reagent 22 to overcome the capillary stop formed at the intersection of channel 19 and mixing chamber 20. The reagent 22 starts flowing into the mixing chamber 20, as illustrated in FIG. 4F. When the reagent 22 meets with the meniscus 25 formed by biological sample fluid 23 at the tip section (capillary port) 16 of the liquid metering tube 15, it breaks the surface tension force at the meniscus 25. The biological sample fluid 23 filled in the liquid metering tube 15 starts flowing into the mixing chamber 20, and mixes with reagent 22, as shown in FIG. 4G, to form a reaction mixture 28.

Figure 4H:
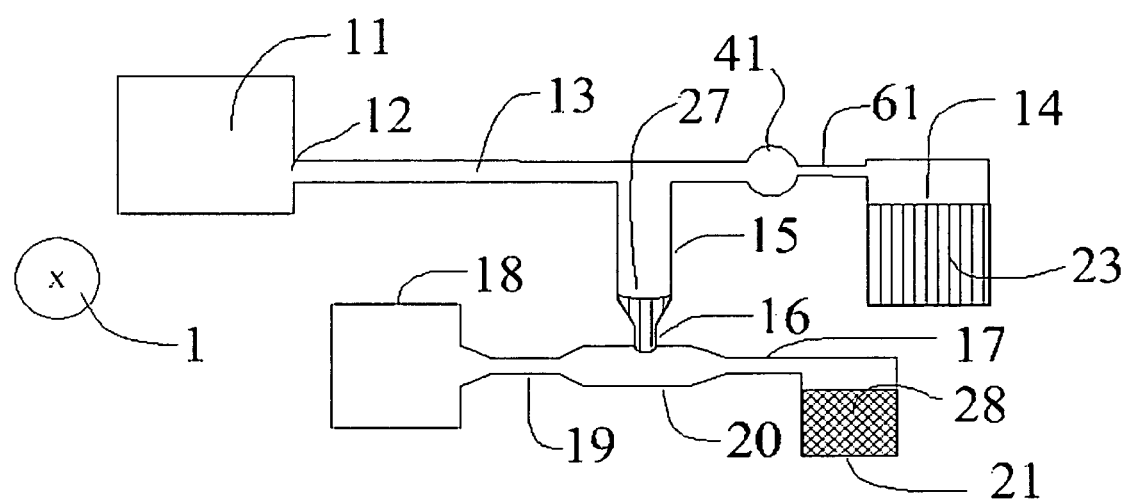
FIG. 4H shows a schematic diagram wherein the reaction mixture of sample and reagent has completely transported to a detection chamber.

As the rotor continues to spin at speed S3, all reagent 22 will be pushed out of the reagent chamber 18 to mix with biological sample fluid 23 in the mixing chamber 20. The reaction mixture 28 will then be driven into the detection chamber 21, as shown in FIG. 4H. In many instances, there will be some biological sample fluid 23 left in the liquid metering tube 15. But the amount of biological sample fluid 23 that was added into the reaction mixture 28 can be precise and consistently repeatable. The amount of sample fluid added can be calculated, e.g., based on the difference in the fluid level 27 and the sample fluid level before S3. Given the volume of pre-packaged reagent 22 is known, the mixing ratio of biological sample fluid 23 and reagent 22 can be determined precisely.

Example 4

Devices with Channels Arranged in a Vertical Plane

Figure 5:
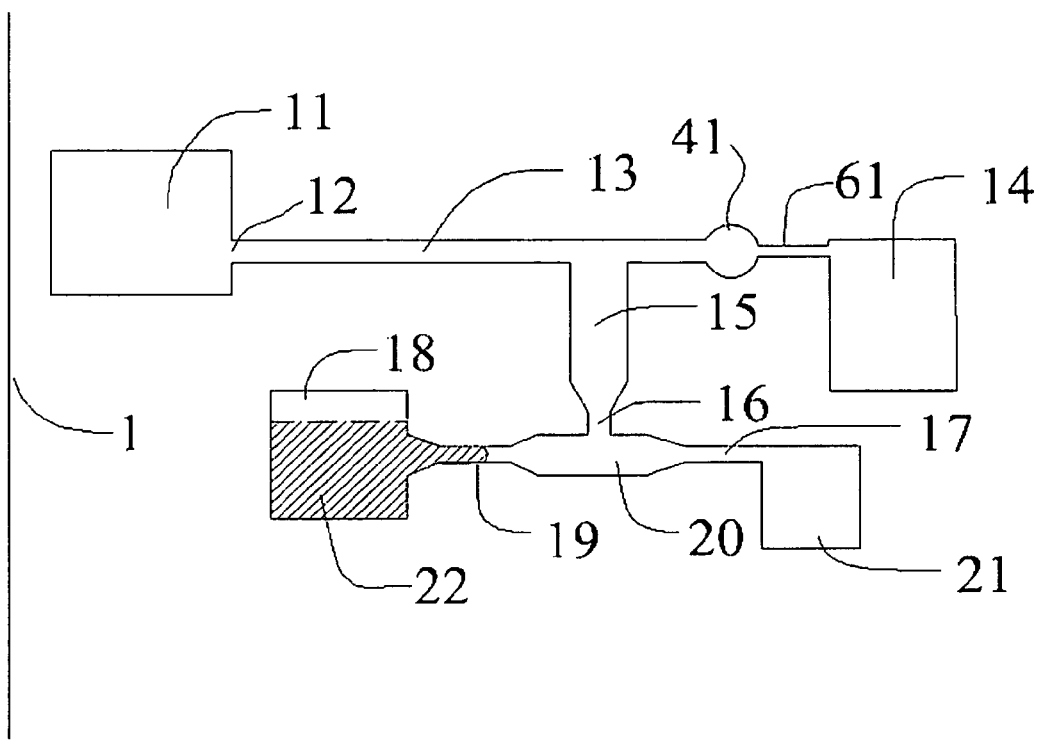
FIG. 5 shows a view of an assay analyzing unit on the centrifugal fluid analyzing rotor wherein the rotational axis is of the rotor is coplanar with the metering tube central axis. That is, the chambers and channels are arranged in a plane parallel to the rotor rotational axis.

According to another preferred embodiment of present invention, the axis of rotation 1 can be in the plane of assay analyzing unit. FIG. 5 shows a vertical cross sectional view of an assay analyzing unit arranged in a vertical plane. The sample chamber 11 and reagent chamber 18 are arranged in different levels of a vertical plane. The liquid metering tube 15 is arranged vertically. Since the capillary force is not affected by the arrangement, the same working principles described in the first preferred embodiment of present invention also apply to the second preferred embodiment of present invention.

In this embodiment, capillary stops should be adjusted, relative to configurations wherein the channels are arranged in a substantially horizontal plane, taking into consideration, e.g., the contributions of gravity to pressures at capillary stop ports. For example, in the vertical layout, the capillary port 16 can be narrower.

Example 5

Rotors for Multiple Samples Assays

Figure 6:
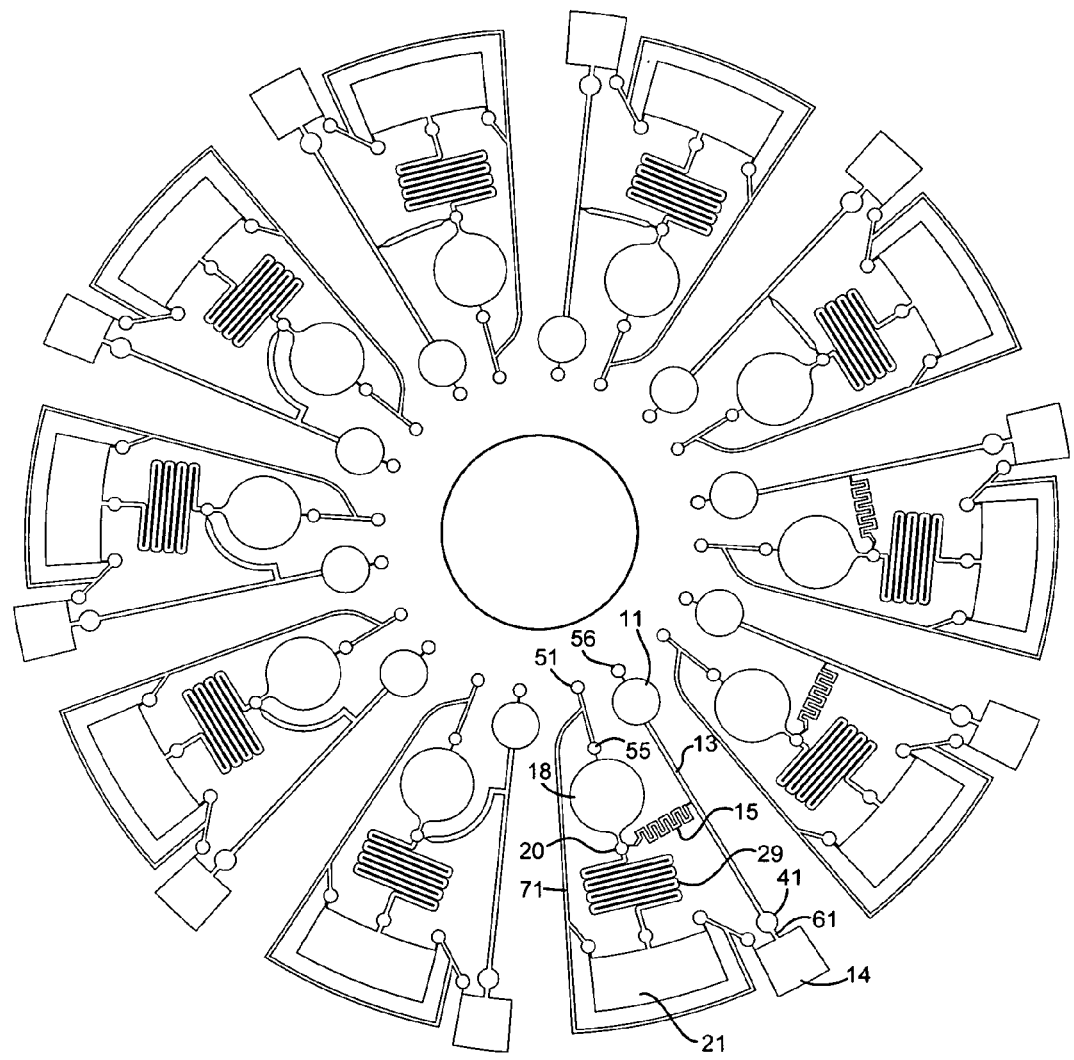
FIG. 6 is an overall plan view of a centrifugal fluid analyzing rotor having various alternate metering tube configurations. The rotor also includes separate sample chambers for each assay unit.

According to a another preferred embodiment of present invention, each assay analyzing unit on the centrifugal fluid analyzing rotor can form an independent channel that has its own sample chamber 11, as shown in FIG. 6. In this configuration, each individual analyzing unit can take different biological sample fluid for assaying. As illustrated in the figure, the shape of liquid metering tube 15 can take different forms. Optionally, the mixing maze can take on any of a variety of configurations, although not illustrated in the figure. In this type of arrangement, a bubble 56 is provided so that when the biological sample fluid moves from the sample chamber 11 to channel 13, there is air ventilation.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, many of the techniques and apparatus described above can be used in various combinations.

All publications, patents, patent applications, and/or other documents cited in this application are incorporated by reference in their entirety for all purposes to the same extent as if each individual publication, patent, patent application, and/or other document were individually indicated to be incorporated by reference.

What is claimed is:

1. A fluid analysis rotor comprising:
   a rotational axis;
   a reagent chamber in fluid contact with a mixing chamber through a reagent conduit; and,
   a sample chamber in fluid contact with the mixing chamber through a metering tube comprising a capillary port at the mixing chamber;
   wherein, the rotor is configured so that when the rotor is not rotating about the axis, a liquid reagent in the reagent chamber does not flow into the mixing chamber through the conduit, and liquid sample in the sample chamber does not flow into the mixing chamber through the capillary port;
   wherein at a first rotor rotation speed, the liquid sample fills the metering tube but is retained from flowing into the mixing chamber by a meniscus surface tension of the liquid sample at the capillary port; and,
   wherein the rotor structure is configured so that at a second rotor rotation speed faster than the first rotation speed, the liquid reagent flows to contact the sample meniscus at the capillary port in the mixing chamber, thus breaking the sample meniscus surface tension so that the sample flows from the metering tube into the mixing chamber.

2. The rotor of claim 1, wherein the capillary port is configured to have a higher capillarity than a capillarity of the mixing chamber.

3. The rotor of claim 1, wherein the metering tube has a longest dimension perpendicular to a radial line perpendicular to the rotational axis.

4. The rotor of claim 1, wherein the reagent chamber is closer to the rotational axis than the metering tube is to the rotational axis.

5. The rotor of claim 1, wherein the reagent conduit comprises a stop valve between the reagent chamber and mixing chamber.

6. The rotor of claim 1, wherein the rotational axis is a vertical axis and the metering tube comprises a horizontal central axis.

7. The rotor of claim 1, wherein the first rotor speed is greater than zero rpm.

8. The rotor of claim 1, wherein a surface tension of the liquid sample at the meter tube capillary port is greater than a surface tension at the reagent conduit stop valve.

* * * * *